(12) United States Patent
Ginn (10) Patent No.: US 8,852,229 B2
(45) Date of Patent: Oct. 7, 2014

(54) LOCATOR AND CLOSURE DEVICE AND METHOD OF USE

(75) Inventor: Richard S. Ginn, San Jose, CA (US)

(73) Assignee: Cordis Corporation

( * ) Notice: Subject to any disclaimer, the term of this patent is extended or adjusted under 35 U.S.C. 154(b) by 704 days.

(21) Appl. No.: 10/687,848

(22) Filed: Oct. 17, 2003

(65) Prior Publication Data

US 2005/0085854 A1 Apr. 21, 2005

(51) Int. Cl.
*A61B 17/08* (2006.01)
*A61D 1/00* (2006.01)
*A61B 17/00* (2006.01)
*A61B 19/00* (2006.01)

(52) U.S. Cl.
CPC ... *A61B 17/0057* (2013.01); *A61B 2017/00654* (2013.01); *A61B 2017/00637* (2013.01); *A61B 2019/4857* (2013.01); *A61B 2019/462* (2013.01); *A61B 2017/00004* (2013.01); *A61B 2017/00022* (2013.01)
USPC .......................................................... 606/213

(58) Field of Classification Search
USPC ................. 606/213, 232, 138–143, 151–158, 606/139–143, 219–221; 623/23.72
See application file for complete search history.

(56) References Cited

U.S. PATENT DOCUMENTS

| 287,046 A | 10/1883 | Norton |
|---|---|---|
| 2,969,887 A | 1/1961 | Darmstadt et al. |
| 3,015,403 A | 1/1962 | Fuller |
| 3,678,158 A | 7/1972 | Sussman |
| 3,683,655 A | 8/1972 | White et al. |
| 3,757,783 A | 9/1973 | Alley |
| 3,875,595 A | 4/1975 | Froning |
| 3,941,127 A | 3/1976 | Froning |
| 3,944,114 A | 3/1976 | Coppens |
| 3,952,377 A | 4/1976 | Morell |
| 3,964,480 A | 6/1976 | Froning |

(Continued)

FOREIGN PATENT DOCUMENTS

| DE | 3922203 C1 | 10/1990 |
|---|---|---|
| DE | 19710392 C1 | 7/1999 |

(Continued)

OTHER PUBLICATIONS

E.H. Cassinelli, M.D., et al., "Biochemistry of Intervertebral Disc Degeneration and the Potential for Gene Therapy Applications", SpineLine, The Clinical & News Magazine for Spine Care Professionals, vol. 11, Issue 1, Jan.-Feb. 2001.

(Continued)

*Primary Examiner* — Melanie Tyson (57) ABSTRACT

An apparatus for sealing a vascular puncture and for properly locating and deploying a sealing member. The apparatus comprises a lumen which extends from an opening in the distal region of the apparatus to another opening in the proximal region of the apparatus. A sealing member is located at the end of the lumen. When the distal opening is positioned within the blood vessel lumen, blood flows through the distal opening, through the lumen and out of the proximal opening indicating that the sealing member is within the blood vessel lumen. When the sealing member is withdrawn from the vessel lumen, it blocks the blood flow into the distal opening. The sealing member may be further withdrawn a predetermined distance so that no part of the sealing member extends into the blood vessel lumen. The sealing device is then detached from the delivery apparatus to seal the vascular puncture.

6 Claims, 9 Drawing Sheets

(56) References Cited

U.S. PATENT DOCUMENTS

| | | | |
|---|---|---|---|
| 4,269,174 A | 5/1981 | Adair | |
| 4,301,802 A | 11/1981 | Poler | |
| 4,439,423 A | 3/1984 | Smith | |
| 4,447,915 A | 5/1984 | Weber | |
| 4,509,233 A | 4/1985 | Shaw | |
| 4,525,157 A | 6/1985 | Vaillancourt | |
| 4,586,502 A | 5/1986 | Bedi et al. | |
| 4,638,799 A | 1/1987 | Moore | |
| 4,719,108 A | 1/1988 | Smith | |
| 4,738,658 A | 4/1988 | Magro et al. | |
| 4,741,330 A | 5/1988 | Hayhurst | |
| 4,741,336 A | 5/1988 | Failla et al. | |
| 4,744,364 A * | 5/1988 | Kensey | 606/213 |
| 4,772,287 A | 9/1988 | Ray et al. | |
| 4,802,478 A | 2/1989 | Powell | |
| 4,852,568 A | 8/1989 | Kensey | |
| 4,863,477 A | 9/1989 | Monson | |
| 4,878,893 A | 11/1989 | Chin | |
| 4,878,915 A | 11/1989 | Brantigan | |
| 4,890,612 A | 1/1990 | Kensey | |
| 4,904,260 A | 2/1990 | Ray et al. | |
| 4,968,298 A | 11/1990 | Michelson | |
| 4,998,934 A | 3/1991 | Bernstein | |
| 5,002,557 A | 3/1991 | Hasson | |
| 5,007,921 A | 4/1991 | Brown | |
| 5,015,247 A | 5/1991 | Michelson | |
| 5,021,059 A | 6/1991 | Kensey et al. | |
| 5,026,390 A | 6/1991 | Brown | |
| 5,032,125 A | 7/1991 | Durham et al. | |
| 5,061,274 A * | 10/1991 | Kensey | 606/213 |
| 5,108,420 A | 4/1992 | Marks | |
| 5,114,032 A | 5/1992 | Laidlaw | |
| 5,123,926 A | 6/1992 | Pisharodi | |
| 5,190,050 A | 3/1993 | Nitzsche | |
| 5,192,301 A * | 3/1993 | Kamiya et al. | 606/213 |
| 5,192,302 A | 3/1993 | Kensey et al. | |
| 5,222,974 A | 6/1993 | Kensey et al. | |
| 5,232,451 A | 8/1993 | Freitas et al. | |
| 5,258,042 A | 11/1993 | Mehta | |
| 5,275,616 A | 1/1994 | Fowler | |
| 5,290,310 A | 3/1994 | Makower et al. | |
| 5,292,332 A * | 3/1994 | Lee | 606/213 |
| 5,304,184 A | 4/1994 | Hathaway et al. | |
| 5,306,234 A | 4/1994 | Johnson | |
| 5,306,254 A | 4/1994 | Nash et al. | |
| 5,312,435 A | 5/1994 | Nash et al. | |
| 5,318,525 A | 6/1994 | West et al. | |
| 5,320,639 A | 6/1994 | Rudnick | |
| 5,334,216 A | 8/1994 | Vidal et al. | |
| 5,334,217 A | 8/1994 | Das | |
| 5,342,393 A | 8/1994 | Stack | |
| 5,383,852 A | 1/1995 | Stevens-Wright | |
| 5,383,905 A | 1/1995 | Golds et al. | |
| RE34,866 E | 2/1995 | Kensey et al. | |
| 5,411,520 A | 5/1995 | Nash et al. | |
| 5,425,757 A | 6/1995 | Tiefenbrun et al. | |
| 5,431,639 A | 7/1995 | Shaw | |
| 5,443,481 A | 8/1995 | Lee | |
| 5,486,195 A | 1/1996 | Myers et al. | |
| 5,492,763 A | 2/1996 | Barry et al. | |
| 5,507,744 A | 4/1996 | Tay et al. | |
| 5,522,840 A | 6/1996 | Krajicek | |
| 5,531,759 A | 7/1996 | Kensey et al. | |
| 5,549,633 A * | 8/1996 | Evans et al. | 606/139 |
| 5,549,679 A | 8/1996 | Kuslich | |
| 5,554,162 A | 9/1996 | Delange | |
| 5,562,736 A | 10/1996 | Ray et al. | |
| 5,571,181 A | 11/1996 | Li | |
| 5,571,189 A | 11/1996 | Kuslich | |
| 5,573,994 A | 11/1996 | Kabra et al. | |
| 5,588,424 A | 12/1996 | Insler et al. | |
| 5,588,992 A | 12/1996 | Scott et al. | |
| 5,591,206 A | 1/1997 | Moufarrege | |
| 5,601,556 A | 2/1997 | Pisharodi | |
| 5,645,565 A | 7/1997 | Rudd et al. | |
| 5,674,296 A | 10/1997 | Bryan et al. | |
| 5,676,689 A * | 10/1997 | Kensey et al. | 606/213 |
| 5,681,334 A * | 10/1997 | Evans et al. | 606/148 |
| 5,690,674 A * | 11/1997 | Diaz | 606/213 |
| 5,702,421 A | 12/1997 | Schneidt | |
| 5,707,352 A | 1/1998 | Sekins et al. | |
| 5,713,911 A | 2/1998 | Racenet | |
| 5,720,748 A | 2/1998 | Kuslich et al. | |
| 5,725,554 A | 3/1998 | Simon et al. | |
| 5,728,116 A | 3/1998 | Rosenman | |
| 5,728,122 A | 3/1998 | Leschinsky et al. | |
| 5,728,132 A * | 3/1998 | Van Tassel et al. | 606/213 |
| 5,728,146 A | 3/1998 | Burkett et al. | |
| 5,741,429 A | 4/1998 | Donadio, III et al. | |
| 5,782,861 A * | 7/1998 | Cragg et al. | 606/216 |
| 5,800,549 A | 9/1998 | Bao et al. | |
| 5,800,550 A | 9/1998 | Sertich | |
| 5,810,810 A | 9/1998 | Tay et al. | |
| 5,814,062 A | 9/1998 | Sepetka et al. | |
| 5,830,125 A | 11/1998 | Scribner et al. | |
| 5,830,171 A | 11/1998 | Wallace | |
| 5,843,124 A * | 12/1998 | Hammerslag | 606/214 |
| 5,853,422 A | 12/1998 | Huebsch et al. | |
| 5,855,601 A | 1/1999 | Bessler et al. | |
| 5,857,999 A | 1/1999 | Quick et al. | |
| 5,861,004 A * | 1/1999 | Kensey et al. | 606/213 |
| 5,865,846 A | 2/1999 | Bryan et al. | |
| 5,871,474 A | 2/1999 | Hermann et al. | |
| 5,871,501 A | 2/1999 | Leschinsky et al. | |
| 5,871,525 A | 2/1999 | Edwards et al. | |
| 5,879,366 A | 3/1999 | Shaw et al. | |
| 5,888,220 A | 3/1999 | Felt et al. | |
| 5,888,223 A | 3/1999 | Bray, Jr. | |
| 5,888,224 A | 3/1999 | Beckers et al. | |
| 5,893,856 A | 4/1999 | Jacob et al. | |
| 5,893,890 A | 4/1999 | Pisharodi | |
| 5,895,411 A | 4/1999 | Irie | |
| 5,897,593 A | 4/1999 | Kohrs et al. | |
| 5,904,648 A | 5/1999 | Arndt et al. | |
| 5,906,631 A | 5/1999 | Imran | |
| 5,908,428 A | 6/1999 | Scirica et al. | |
| 5,919,200 A | 7/1999 | Stambaugh et al. | |
| 5,921,994 A * | 7/1999 | Andreas et al. | 606/144 |
| 5,941,899 A | 8/1999 | Granger et al. | |
| 5,944,738 A | 8/1999 | Amplatz et al. | |
| 5,954,636 A | 9/1999 | Schwartz et al. | |
| 5,954,766 A | 9/1999 | Zadno-Azizi et al. | |
| 5,964,807 A | 10/1999 | Gan et al. | |
| 5,972,015 A | 10/1999 | Scribner et al. | |
| 5,972,031 A | 10/1999 | Biedermann et al. | |
| 5,984,927 A | 11/1999 | Wenstrom, Jr. et al. | |
| 5,989,230 A | 11/1999 | Frassica | |
| 6,001,130 A | 12/1999 | Bryan et al. | |
| 6,003,517 A | 12/1999 | Sheffield et al. | |
| 6,007,563 A * | 12/1999 | Nash et al. | 606/213 |
| 6,007,570 A | 12/1999 | Sharkey et al. | |
| 6,013,052 A | 1/2000 | Durman et al. | |
| 6,016,806 A | 1/2000 | Webb | |
| 6,020,380 A | 2/2000 | Killian | |
| 6,022,376 A | 2/2000 | Assell et al. | |
| 6,027,525 A | 2/2000 | Suh et al. | |
| 6,030,442 A | 2/2000 | Kabra et al. | |
| 6,033,427 A | 3/2000 | Lee | |
| 6,036,720 A | 3/2000 | Abrams et al. | |
| 6,048,346 A | 4/2000 | Reiley et al. | |
| 6,056,749 A | 5/2000 | Kuslich | |
| 6,056,768 A | 5/2000 | Cates et al. | |
| 6,066,108 A | 5/2000 | Lundberg | |
| 6,066,154 A | 5/2000 | Reiley et al. | |
| 6,071,292 A | 6/2000 | Makower et al. | |
| 6,077,281 A | 6/2000 | Das | |
| 6,077,291 A | 6/2000 | Das | |
| 6,080,182 A | 6/2000 | Shaw et al. | |
| 6,082,362 A | 7/2000 | Webb | |
| 6,086,608 A | 7/2000 | Ek et al. | |
| 6,093,207 A | 7/2000 | Pisharodi | |
| 6,095,149 A | 8/2000 | Sharkey et al. | |
| 6,099,567 A | 8/2000 | Badylak et al. | |
| 6,122,549 A | 9/2000 | Sharkey et al. | |

(56) References Cited

U.S. PATENT DOCUMENTS

| | | | |
|---|---|---|---|
| 6,126,675 A | 10/2000 | Shchervinsky et al. | |
| 6,126,682 A | 10/2000 | Sharkey et al. | |
| 6,143,004 A | 11/2000 | Davis et al. | |
| 6,146,380 A | 11/2000 | Racz et al. | |
| 6,146,419 A | 11/2000 | Eaton | |
| 6,156,067 A | 12/2000 | Bryan et al. | |
| 6,162,240 A | 12/2000 | Cates et al. | |
| 6,174,322 B1 | 1/2001 | Schneidt | |
| 6,174,323 B1 | 1/2001 | Biggs et al. | |
| 6,183,518 B1 | 2/2001 | Ross et al. | |
| 6,197,042 B1 * | 3/2001 | Ginn et al. | 606/213 |
| 6,206,907 B1 | 3/2001 | Marino et al. | |
| 6,206,921 B1 | 3/2001 | Guagliano et al. | |
| 6,206,922 B1 | 3/2001 | Zdeblich et al. | |
| 6,206,923 B1 | 3/2001 | Boyd et al. | |
| 6,221,109 B1 | 4/2001 | Geistlich et al. | |
| 6,231,561 B1 | 5/2001 | Frazier et al. | |
| 6,240,849 B1 | 6/2001 | Holler | |
| 6,248,131 B1 | 6/2001 | Felt et al. | |
| 6,258,100 B1 | 7/2001 | Alferness et al. | |
| 6,270,515 B1 | 8/2001 | Linden et al. | |
| 6,287,290 B1 | 9/2001 | Perkins et al. | |
| 6,290,674 B1 | 9/2001 | Roue et al. | |
| 6,293,951 B1 | 9/2001 | Alferness et al. | |
| 6,296,657 B1 | 10/2001 | Brucker | |
| 6,302,898 B1 | 10/2001 | Edwards et al. | |
| 6,306,114 B1 | 10/2001 | Freeman et al. | |
| 6,319,263 B1 | 11/2001 | Levinson | |
| 6,327,505 B1 | 12/2001 | Medhkour et al. | |
| 6,346,112 B2 | 2/2002 | Adams | |
| 6,348,064 B1 | 2/2002 | Kanner | |
| 6,350,274 B1 * | 2/2002 | Li | 606/213 |
| 6,368,341 B1 | 4/2002 | Abrahamson | |
| 6,379,368 B1 | 4/2002 | Corcoran et al. | |
| 6,447,539 B1 | 9/2002 | Nelson et al. | |
| 6,458,100 B2 | 10/2002 | Roue et al. | |
| 6,464,645 B1 | 10/2002 | Park et al. | |
| 6,482,224 B1 | 11/2002 | Michler et al. | |
| 6,482,235 B1 | 11/2002 | Lambrecht et al. | |
| 6,494,848 B1 | 12/2002 | Sommercorn et al. | |
| 6,517,559 B1 | 2/2003 | O'Connell | |
| 6,547,810 B1 | 4/2003 | Sharkey et al. | |
| 6,554,833 B2 | 4/2003 | Levy et al. | |
| 6,626,918 B1 * | 9/2003 | Ginn et al. | 606/148 |
| 6,645,225 B1 | 11/2003 | Atkinson | |
| 6,656,206 B2 | 12/2003 | Corcoran et al. | |
| 6,663,655 B2 | 12/2003 | Ginn et al. | |
| 6,682,489 B2 * | 1/2004 | Tenerz et al. | 600/485 |
| 6,695,867 B2 * | 2/2004 | Ginn et al. | 606/213 |
| 6,699,261 B1 | 3/2004 | Cates et al. | |
| 6,702,835 B2 | 3/2004 | Ginn | |
| 6,716,179 B2 | 4/2004 | Burbank et al. | |
| 6,776,784 B2 | 8/2004 | Ginn | |
| 6,846,319 B2 | 1/2005 | Ginn et al. | |
| 6,860,895 B1 | 3/2005 | Akerfeldt et al. | |
| 7,008,439 B1 | 3/2006 | Janzen et al. | |
| 7,144,411 B2 * | 12/2006 | Ginn et al. | 606/213 |
| 7,317,951 B2 | 1/2008 | Schneider et al. | |
| 7,361,183 B2 | 4/2008 | Ginn | |
| 2001/0003158 A1 * | 6/2001 | Kensey et al. | 606/213 |
| 2001/0037808 A1 | 11/2001 | Deem et al. | |
| 2001/0052344 A1 | 12/2001 | Doshi | |
| 2002/0002386 A1 | 1/2002 | Ginn et al. | |
| 2002/0016583 A1 | 2/2002 | Cragg | |
| 2002/0022822 A1 * | 2/2002 | Cragg et al. | 604/500 |
| 2002/0072767 A1 * | 6/2002 | Zhu | 606/213 |
| 2002/0077656 A1 * | 6/2002 | Ginn et al. | 606/213 |
| 2002/0077657 A1 | 6/2002 | Ginn et al. | |
| 2002/0077658 A1 | 6/2002 | Ginn | |
| 2002/0077701 A1 | 6/2002 | Kuslich | |
| 2002/0082617 A1 | 6/2002 | Nishtala et al. | |
| 2002/0095179 A1 * | 7/2002 | Tenerz et al. | 606/213 |
| 2002/0112729 A1 | 8/2002 | DeVore et al. | |
| 2002/0183787 A1 | 12/2002 | Wahr et al. | |
| 2003/0023267 A1 | 1/2003 | Ginn | |
| 2003/0033006 A1 | 2/2003 | Phillips et al. | |
| 2003/0045893 A1 | 3/2003 | Ginn | |
| 2003/0050665 A1 | 3/2003 | Ginn | |
| 2003/0088271 A1 * | 5/2003 | Cragg et al. | 606/213 |
| 2003/0139819 A1 | 7/2003 | Beer et al. | |
| 2003/0144694 A1 | 7/2003 | Chanduszko et al. | |
| 2003/0145865 A1 | 8/2003 | Sterman et al. | |
| 2003/0208232 A1 | 11/2003 | Blaeser et al. | |
| 2003/0225421 A1 | 12/2003 | Peavey et al. | |
| 2004/0019330 A1 | 1/2004 | Ashby | |
| 2004/0059375 A1 * | 3/2004 | Ginn et al. | 606/213 |
| 2004/0073242 A1 | 4/2004 | Chanduszko | |
| 2004/0098042 A1 | 5/2004 | Devellian et al. | |
| 2004/0098121 A1 | 5/2004 | Opolski | |
| 2004/0133236 A1 | 7/2004 | Chanduszko | |
| 2004/0158287 A1 * | 8/2004 | Cragg et al. | 606/213 |
| 2004/0204654 A1 | 10/2004 | Egnelov et al. | |
| 2004/0215232 A1 * | 10/2004 | Belhe et al. | 606/213 |
| 2005/0065549 A1 | 3/2005 | Cates et al. | |
| 2005/0085854 A1 | 4/2005 | Ginn | |
| 2005/0085856 A1 | 4/2005 | Ginn | |
| 2005/0192606 A1 | 9/2005 | Paul et al. | |
| 2005/0267528 A1 | 12/2005 | Ginn et al. | |

FOREIGN PATENT DOCUMENTS

| | | |
|---|---|---|
| EP | 0432321 B1 | 6/1991 |
| EP | 0647430 | 4/1995 |
| EP | 0700671 A1 | 3/1996 |
| EP | 1033115 A2 | 9/2000 |
| EP | 1078601 A2 | 2/2001 |
| FR | 2639823 | 6/1990 |
| WO | WO 92/05828 | 4/1992 |
| WO | WO 93/08740 | 5/1993 |
| WO | WO 95/05206 | 2/1995 |
| WO | WO 97/26847 | 7/1997 |
| WO | WO 98/02100 | 1/1998 |
| WO | WO 98/19605 A | 5/1998 |
| WO | WO 98/20939 | 5/1998 |
| WO | WO 98/48706 | 11/1998 |
| WO | WO 99/02100 | 1/1999 |
| WO | WO 99/02108 | 1/1999 |
| WO | WO 99/02214 | 1/1999 |
| WO | WO 99/61084 | 12/1999 |
| WO | WO 99/65544 | 12/1999 |
| WO | WO 00/07506 | 2/2000 |
| WO | WO 00/62699 | 10/2000 |
| WO | WO 00/69374 | 11/2000 |
| WO | WO 00/71032 | 11/2000 |
| WO | WO 01/02042 A1 | 1/2001 |
| WO | WO 01/10316 A1 | 2/2001 |
| WO | WO 01/13839 A1 | 3/2001 |
| WO | WO 01/13908 A2 | 3/2001 |
| WO | WO 01/21247 A1 | 3/2001 |
| WO | WO 01/26588 A2 | 4/2001 |
| WO | WO 01/28464 A1 | 4/2001 |
| WO | WO 01/45577 A2 | 6/2001 |
| WO | WO 01/45579 A1 | 6/2001 |
| WO | WO 01/60288 A1 | 8/2001 |
| WO | WO 01/66045 A1 | 9/2001 |
| WO | WO 01/66190 A2 | 9/2001 |
| WO | WO 01/87170 A1 | 11/2001 |
| WO | WO 03/047434 A1 | 6/2003 |

OTHER PUBLICATIONS

K. Nishimura, M.D., et al., "Percutaneous Reinsertion of the Nucleus Pulposus", An Experimental Study, Spine vol. 23, No. 14, pp. 1531-1539, 1998.

Maurice Hiles, "New Specialty Polymer Products Through Interpenetrating Polymer Network (IPN) Technology—The Development of an Interpenetrating Polymer Network to Contain Mechanically Induced Vibration", Oct. 20-21, 1986, Colony Square Hotel, Atlanta, GA.

Zoltan G. Turi, M.D., "Overview of Vascular Closure", Endovascular Today, Closure Update 2008, pp. 28-37.

* cited by examiner

FIG. 13

LOCATOR AND CLOSURE DEVICE AND METHOD OF USE

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering such devices.

BACKGROUND OF THE INVENTION

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a-blood vessel or other subcutaneous region.

Various methods and means for determining the location of the distal end of a closure device have been proposed, including "bleedback" methodology such as that disclosed in U.S. Pat. No. 4,738,658 issued to Magro et al. However, prior bleedback devices have been constructed such that blood flow out of the patient continues for a longer period of time during deployment of the sealing means than would be desirable. Thus, a need exists for a closure device with a bleedback locator feature which reduces the amount of time during which blood flows out of the patient during deployment of a sealing member.

SUMMARY OF INVENTION

The present invention is directed to a device which is capable of both locating a punctured blood vessel and sealing the puncture in the vessel and to the method of using the device as well. This device makes use of a "bleed back" feature, but, unlike known bleed back devices, uses a shut-off feature to deploy a sealing element at the desired location. In a preferred embodiment, the device of the present invention comprises an elongate member having a lumen extending from a point in the distal region to a point in its proximal region. The lumen is connected at its proximal and distal regions to proximal and distal ports in the elongate member which create a conduit from the lumen to the outer surface of the elongate member. In this embodiment, the elongate member is also provided with a detachable sealing element which is attached to the elongate member distally of its distal port. The sealing element may be a bioabsorbable felt or other suitable material. The proximal and distal ports are spaced sufficiently far apart that the proximal port is outside the patient's body when the distal port is within the lumen of the punctured blood vessel.

In an alternative embodiment, a groove in the outer wall of the elongate member or in the inner wall of a tubular member, such as an introducer sheath, which runs from the distal region of the elongate member to the proximal region thereof is provided proximal to the sealing element such that blood can flow through the groove when the distal end of the groove is in communication with the blood in a blood vessel.

In use, the device of the present invention can be used to close a puncture wound such as that in a femoral artery after a catheterization procedure has been performed. Typically, the device of the present invention will be introduced through an introducer sheath used in the catheterization procedure. When so used, the device is passed through the introducer sheath until the sealing element of its distal end and the distal port or distal opening of a groove are within the lumen of the femoral artery. The user will know when this has occurred when blood emerges from the proximal port or proximal end of a groove since this will occur when the distal port or distal end of a groove reaches the lumen of a blood vessel such as the femoral artery. Once this occurs, the device is withdrawn a short distance until the sealing element is no longer within the lumen of the femoral artery.

The user will know when the sealing element is no longer within the lumen of the femoral artery because the blood flow out of the proximal port or proximal end of a groove will cease or substantially diminish once the sealing element is outside of the lumen of the femoral artery and is substantially sealing the puncture wound. In this preferred embodiment, the sealing element is fabricated from an expandable material which then expands to assure an effective closure of the puncture wound.

The foregoing description has been directed to sealing a puncture wound in the femoral artery, but it is to be understood that the device of the present invention can be used to locate the lumens of other blood vessels and to seal puncture wounds in them. With that understanding, we turn to a more detailed description of the invention.

DETAILED DESCRIPTION OF THE INVENTION

Figure 1:
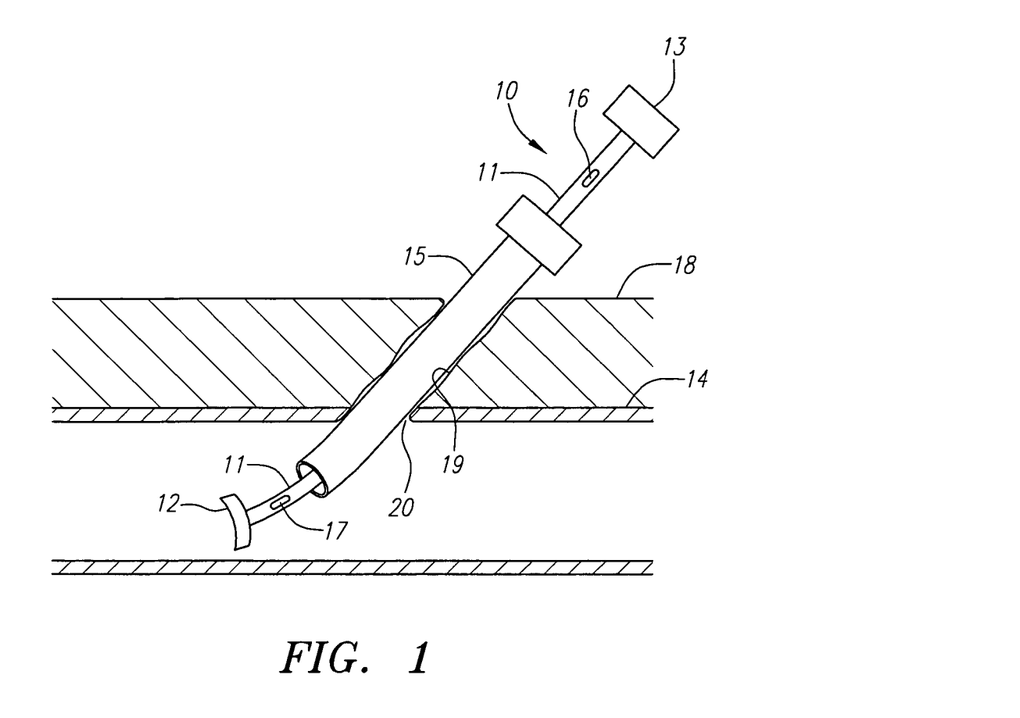
FIG. 1 illustrates the device of the present invention with its distal portion in the lumen of a blood vessel.

As can be seen from FIG. 1, the combined locator-sealing device of the present invention comprises tubular elongated member 11, sealing member 12, and optimally, handle 13. The device 10 is shown as it would be when initially installed with its distal region in the lumen of blood vessel. As shown, the device 10 has been introduced through introducer sheath 15 which may have been used in a previous catheterization procedure.

The elongated member 11 of device 10 has an internal lumen (not shown) which communicates with proximal port 16 and with distal port 17. The proximal port 16 is separated from distal port 17 sufficiently to permit proximal port 16 to be outside of the patient's body when distal port 17 is within the lumen of blood vessel 14. Thus, as shown in FIG. 1, the proximal port 16 is proximal of the patient's skin 18 and device 10 extends through introducer sheath 15 which is located in puncture wound tract 19 and extends through puncture 20 in the wall of the vessel 14.

Figure 2:
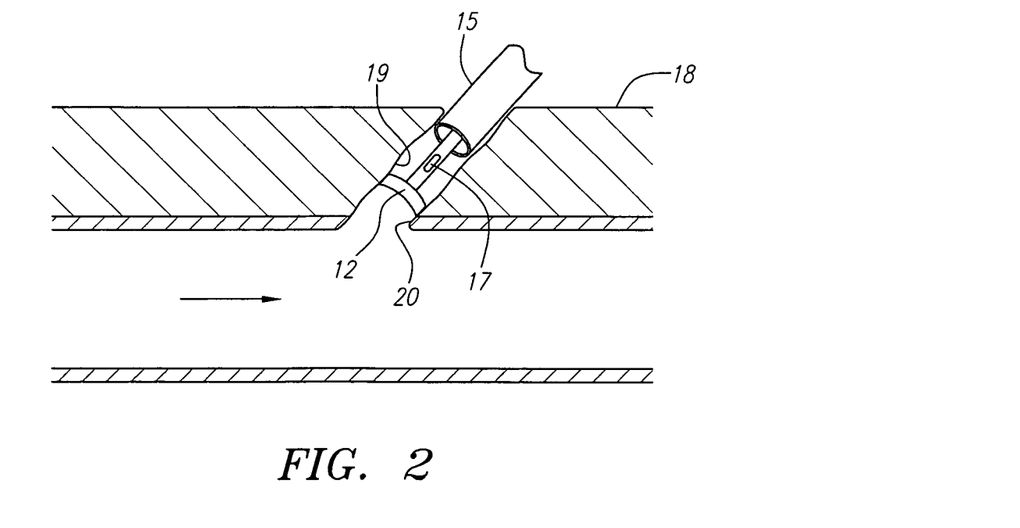
FIG. 2 illustrates the distal region of the device after its distal portion has been withdrawn from the lumen of the blood vessel.

When the device 10 is positioned as shown in FIG. 1, blood will flow into port 17 and out of port 16, thereby indicating that the distal region of device 10, including sealing member 12, is within the lumen of vessel 14. Once it is thus established that distal port 17 and sealing member 12 are within the lumen of vessel 14, the introducer sheath 15 is partially withdrawn as shown in FIG. 2. Device 10 is then withdrawn until, as shown in FIG. 2, sealing member 12 has been withdrawn until it substantially occludes the flow of blood out of vessel 14 through puncture 20. It will be apparent that such occlusion has occurred when the blood flow out of proximal port 16 has been substantially diminished by reason of the occlusion of puncture 20 by sealing member 12. Sealing member 12 is then detached from elongated member 11, as shown in FIG. 3.

Preferably, sealing member 12 will be substantially adjacent to puncture 20 when it is detached. However, the device 10 can be used successfully when sealing member 12 is detached proximally of puncture 20 within tract 19.

Figure 3:
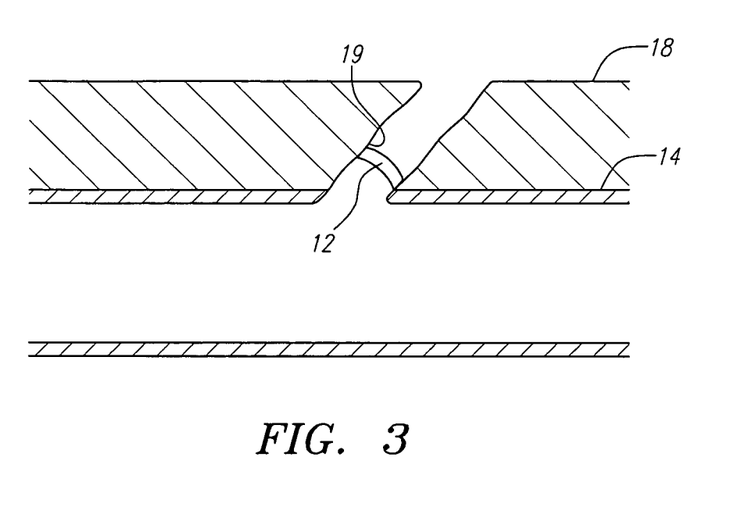
FIG. 3 illustrates the deployed sealing element after it has been detached from the elongate member.

Referring now to FIG. 3, it can be seen that, after disengagement from elongated member 11, sealing member 12 occludes blood flow from puncture 20. In a preferred embodiment, the sealing member 12 will be fabricated from a material which expands upon contact with blood such as a felt made from polyglycolic acid and/or polylactic acid polymers or copolymers or other materials such as collagens. The sealing member 12 may also have one or more hemostasis, antibiotic or other therapeutic agents added to it.

Alternatively, in other preferred embodiments, the sealing member will be made in such a manner that it will expand spontaneously or upon removal of a restraining force. In still other embodiments, the sealing member can be expandable mechanically, hydraulically or pneumatically. In all such embodiments, it is preferred that the sealing member be fabricated from a bioabsorbable material.

Figure 4:
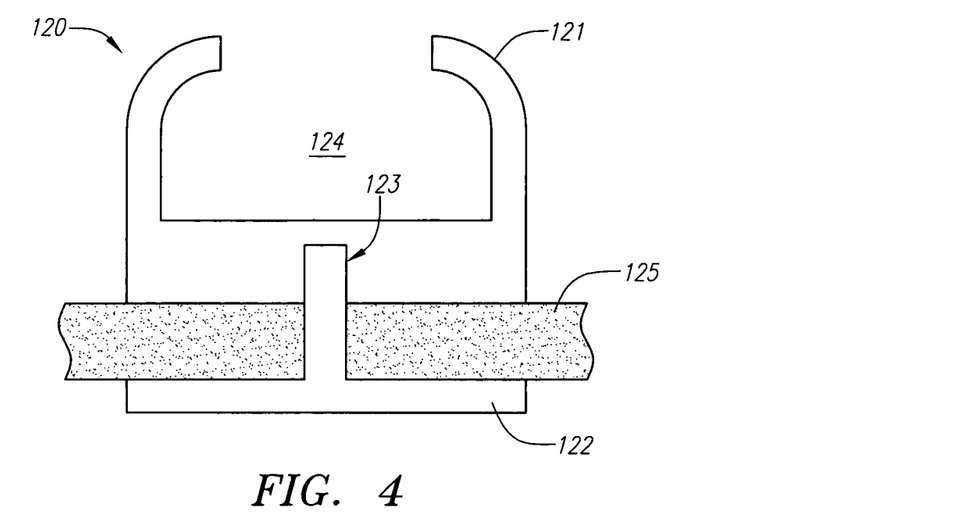
FIGS. 4 and 4A illustrate plug assemblies which may be used according to the present invention.

In FIG. 4, a preferred plug construction is shown. Plug assembly 120 comprises proximal element 121 and distal element 122 which is connected to element 121 through any suitable connection 123. In this embodiment, the connection between elements 121 and 122 is a threaded connection. Proximal element 121 has cavity 124 therein. The purpose of cavity 124 will be explained with regard to FIG. 5. The sealing element of this preferred embodiment is bioabsorbable felt 125. This bioabsorbable felt may be fabricated from polymers of polyglycolic acid, polylactic acid or copolymers thereof.

Figure 4A:
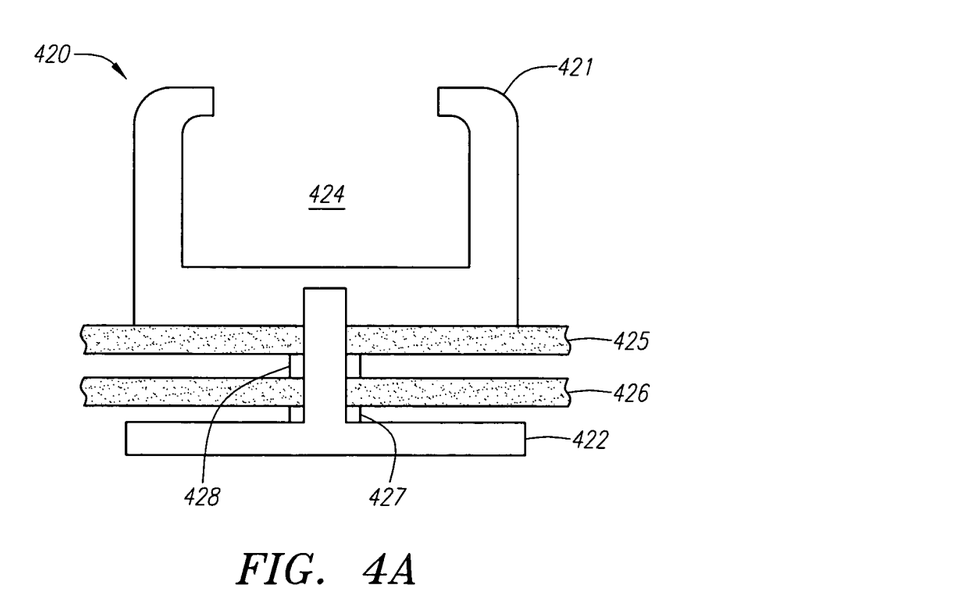

In FIG. 4A, an alternate plug assembly which is provided with two bioabsorbable felt sealing means is illustrated. As shown in FIG. 4A, the plug assembly 420 comprises a proximal portion 421 and a distal portion 422. The plug assembly is provided with two bioabsorbable felt sealing means 425 and 426 which are mounted between proximal portion 421 and distal portion 422. Spacers 427 and 428 are also provided. The additional bioabsorbable felt member increases the efficiency of the sealing function of the plug assembly. It will be readily apparent to those skilled in the art that other configurations of the plug and the sealing elements may be used.

Figure 5:
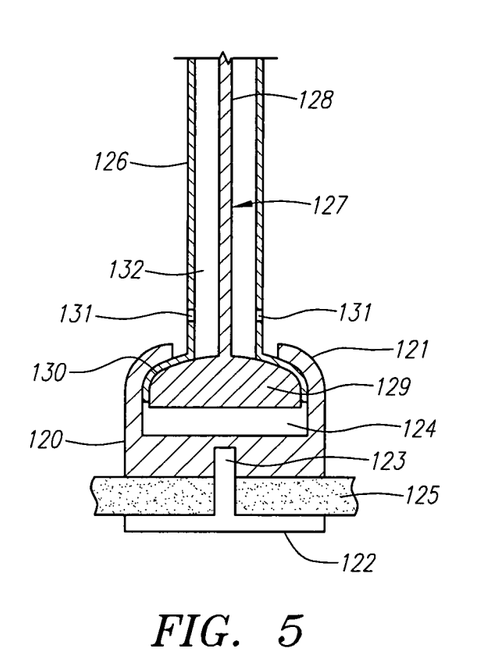
FIG. 5 illustrates the plug assembly in conjunction with a delivery system.

The detachable connections between the sealing member 12 and the elongate member 11 may be any of a wide variety of connections. A preferred connection is illustrated in FIG. 5. In FIG. 5, plug assembly 120 is shown in combination with tubing 126 and pusher 127 which has a proximal shaft 128 and a larger diameter distal region 129 which distal region has a proximal shoulder 130. When it is desired to separate plug assembly 120 from the remainder of the apparatus, pusher 127 is pushed distally (downwardly in FIG. 5) while restraining tubing 126 from movement to push the proximal portion 121 of plug assembly 120 past the outwardly flaring shoulder 130 and the distal region of tubing 126. In this embodiment, tubing 126 is provided with one or more openings 131 in its distal region which communicate with blood flow lumen 132 which, as explained with regard to FIGS. 1 and 2, extends to an opening (not shown in FIG. 5) in the proximal region of sheath 126. Once plug assembly 120 has been detached from sheath 126, pusher 127 is withdrawn from plug assembly 120 simply by pulling pusher 127 in the proximal direction.

Figure 6:
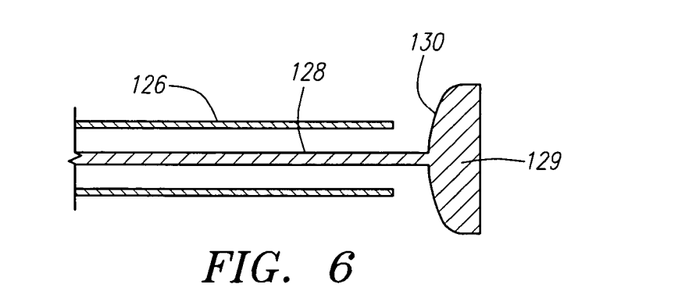
FIG. 6 and 7 illustrate the manner in which elements of the delivery system are coupled to each other.
Figure 7:
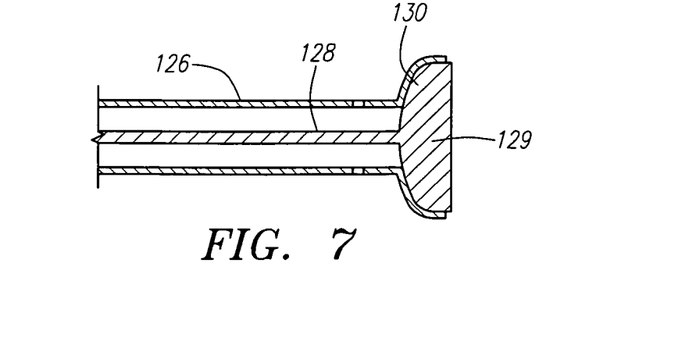

FIGS. 6 and 7 illustrate one manner in which pusher member 127 can be combined with tubing 126. As shown in FIG. 6, tubing 126 is a plastic tube and pusher 127 comprises enlarged distal portion 129 and elongated shaft 128. To assemble these elements, pusher 127 can be moved proximally (to the left as shown in FIG. 6) while tubing 26 is held stationary. The result, as shown in FIG. 7, is that the distal portion of tubing 126 will be expanded by the proximal shoulder 130 on distal portion 129 of pusher 127 such that pusher 127 and tubing 126 are releasably attached to each other. For purposes of simplicity, opening 131 and lumen 132 are not shown in FIGS. 6 and 7.

Accordingly, the structure of FIG. 5 can be assembled by first inserting the distal end 129 of pusher 127 into cavity 124 in plug assembly 120. The outside diameter of distal end 129 is preferably smaller than the inside diameter of the opening in the proximal end 122 of the plug. The tubing 126 is then passed down over shaft 128 into the plug assembly. The tubing 126 is then pushed over the distal portion 129 of the pusher such that the diameter of the tubing expands over the shoulder 130 and distal portion 129. When this is done, the tubing is expanded such that it is larger in outside diameter than the opening in the proximal portion 121 of plug assembly 120. This couples tubing 126 and pusher 127 to plug assembly 120.

To release the plug assembly 120 from tubing 126 and pusher 127, shaft 128 is pushed towards the plug assembly 120 while restraining movement of the tubing 126. The distal portion 129 of pusher 127 is thus pushed out of the expanded end of tubing 126, allowing the tubing to recover to its original outside diameter and to pass through the opening in the proximal portion of 121 of plug assembly 120. Distal portion 129 of pusher 127 is thereby caused to move until it comes into contact with the floor of cavity 124 thereby assisting in pushing the plug off the end of the tubing 126.

Figure 8:
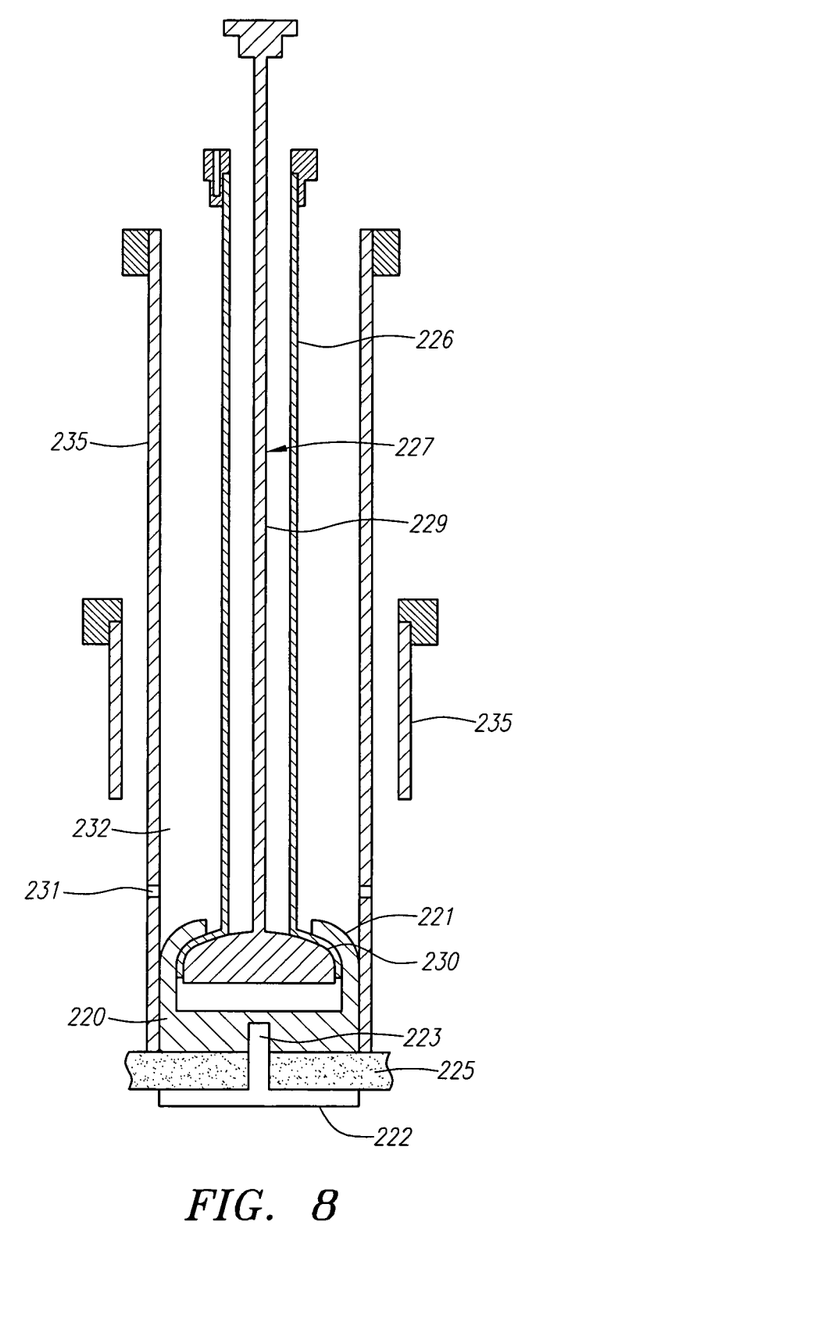
FIG. 8 illustrates in greater detail a delivery system which can be used according to the present invention.

FIG. 8 illustrates additional elements in the delivery system of the present invention. As shown in FIG. 8, plug assembly 220 is releasably attached to detachment assembly 227 as described with regard to FIGS. 5-8. Thus, plug assembly 220 comprises proximal portion 221 and distal portion 222 with a sealing material such as a bioabsorbable felt 225 firmly held between them. Distal portion 222 is attached to proximal portion 221 through any suitable connection 223 such as a threaded connection. Detachment assembly 227 comprises detachment tubing 226 which its distal region flared over shoulder 230 and which is releasably attached to pusher element 229.

Figure 14:
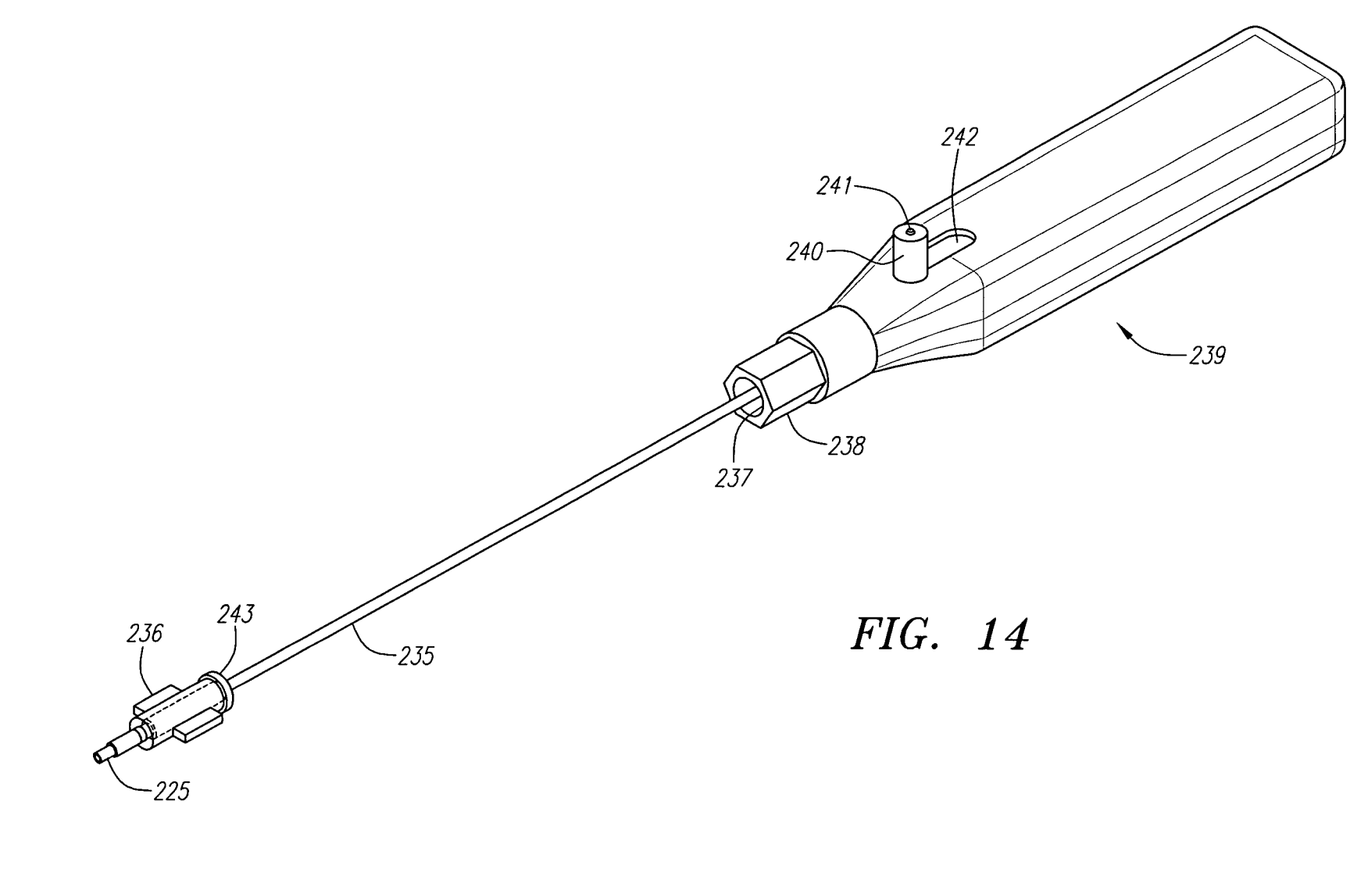
FIG. 14 is a perspective view of the delivery system and plug assembly mounted on a handle.

In this embodiment, detachment assembly 227 is loaded into delivery sheath 235. Delivery sheath 235 is provided with one or more bleed back openings 231 in its distal region. Bleed back opening 231 communicate with lumen 232 through which blood entering openings 231 will flow and, in this embodiment, exit through the proximal end of delivery sheath 235. As shown in FIG. 14 and as further described with regard that Figures lumen 232 may communicate with a handle and outlet port. In addition, delivery sheath 235 may be provided with plug introducer 236 which is shown diagrammatically and which is adapted to slide over plug assembly 220 to capture and compress felt 225 to facilitate introduction of the plug assembly into a femoral sheath which will be described in other figures.

Figure 9:
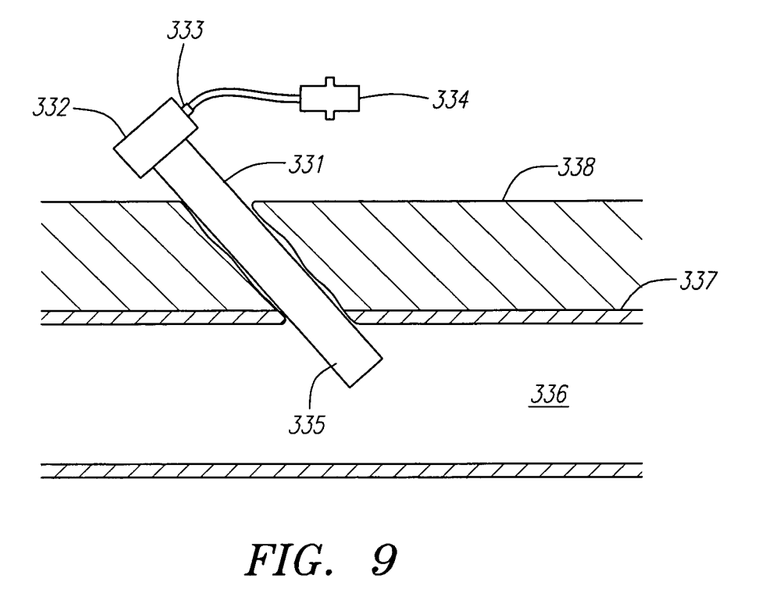
FIGS. 9 through 13 sequentially illustrate the manner in which the locating device and plug assembly of the present invention may be used.

As shown in FIG. 9, femoral, or introducer, sheath 331 having hub 332 and port 333 to which tubing/valve assembly 334 are attached is shown diagrammatically as installed in a patient such that the distal end of femoral sheath 331 extends into the lumen 336 of blood vessel 337. The proximal end of the femoral sheath having hub 332 extends proximally of the patient's skin 338. FIG. 10 illustrates, again diagramatically, the femoral sheath 331 with a delivery sheath 339 of the type described in FIG. 8 together with its associated plug delivery assembly extending part of the way down the femoral sheath, but not yet in the lumen 336 of blood vessel 337. The plug is shown diagramatically as element 340 and the delivery sheath as element 341.

Figure 11:
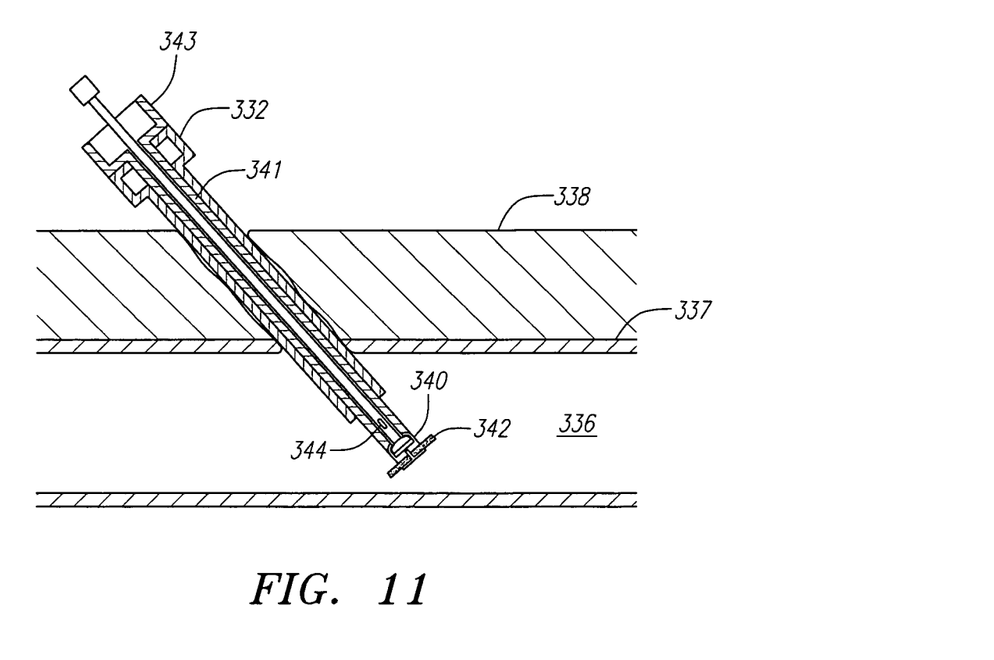
Figure 12:
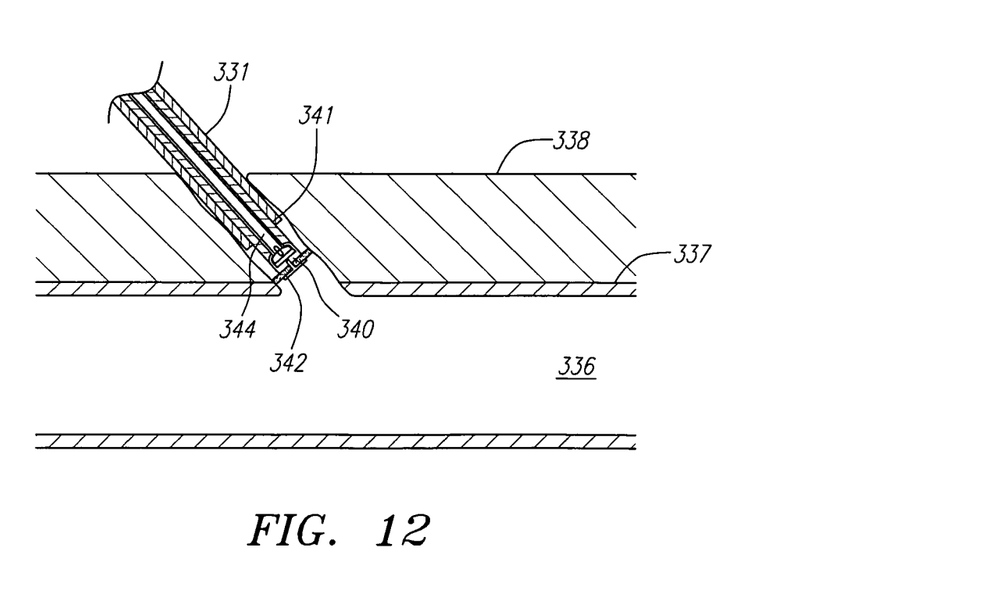

FIG. 11 illustrates the advancement of plug 340 and delivery sheath 341 into blood vessel lumen 336. As shown in FIG. 11, bioabsorbable felt 342 has been released from the plug introducer 236 shown in FIG. 8 and extends radially outwardly from plug 340. As also shown in this figure, the hub 343 of delivery sheath 341 has been advanced until it contacts the hub 332 of femoral sheath 331. When so deployed, one or more bleed back holes 344 are exposed in lumen 336 and permit blood flow through the bleed back lumen in the delivery sheath which is shown as element 232 in FIG. 8. FIG. 12 diagramatically illustrates withdrawal of the femoral sheath and plug assembly into the tissue tract such that the blood flow into the one or more holes 344 in the wall of the delivery sheath has been stopped thereby indicating that the plug assembly is substantially withdrawn from the lumen 336.

Figure 13:
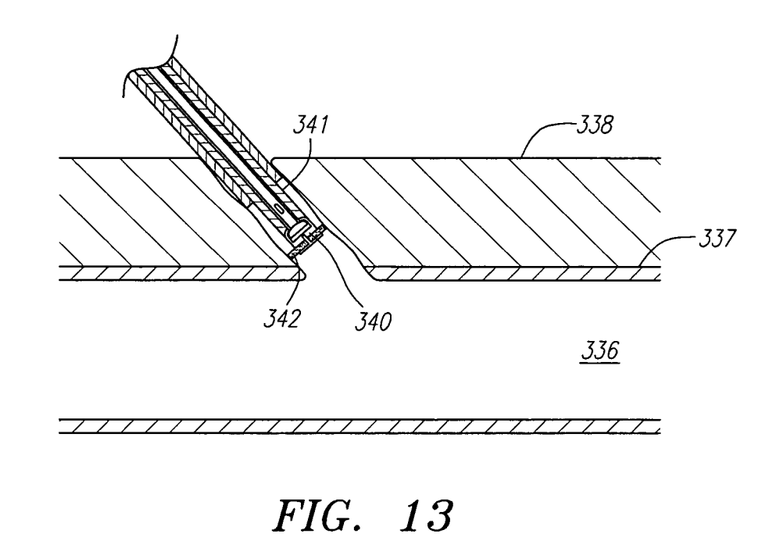

As illustrated in FIG. 13, the plug assembly is then further withdrawn a predetermined fixed amount to assure that no part of the plug assembly is any longer within the lumen 336 of blood vessel 337.

Figure 10:
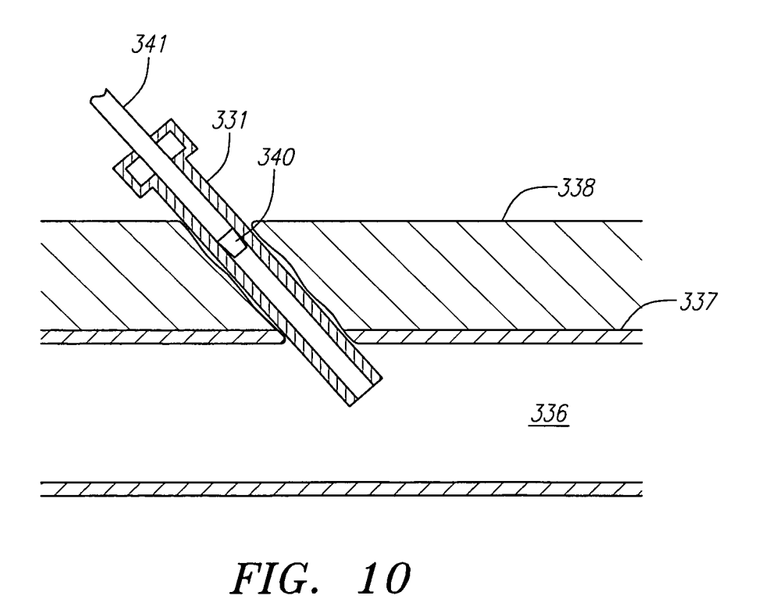

The use of the embodiment illustrated in FIG. 8 is illustrated in FIGS. 9-13. As shown in FIG. 9, a femoral sheath 331 has been inserted for the purpose of facilitating a treatment of a patient such as an angioplasty. After the angioplasty or other procedure has been completed, the device of the present invention is used to seal the puncture in the wall of the blood vessel 337. FIG. 9 shows the femoral sheath 331 in place. FIG. 10 shows the initial stage of advancing the delivery sheath 341 and plug 340 which are shown diagramatically and correspond to plug assembly 220 and delivery sheath 235 of FIG. 8, respectively.

FIG. 11 shows delivery sheath 341 advanced out of the distal end of the femoral sheath such that one or more bleed black holes 344 are exposed to the blood flow in the lumen 336 of blood vessel 337. As also shown, the bioabsorbable felt 341 (which corresponds to felt 225 of FIG. 8) is no longer constrained by the plug introducer shown as element 235 in FIG. 8 and is free to extend radially from plug 340. At this stage of use, the user will know that the plug 340 is in the lumen 336 because the blood flow into one or more holes 344 and through the lumen shown as element 232 in FIG. 8, which blood flow can be observed at the proximal end of the delivery sheath will inform the user that the plug is in the lumen. In a preferred embodiment lumen 232 communicates with outlet tube 240 having port 241 mounted in handle 239 as described in more detail with regard to FIG. 14. The plug has a shoulder, shown as element 230 in FIG. 8, which facilitates locating the tip of the plug in the end of the delivery sheath. The proximal end of detachment tubing 226 is locked into the proximal end of the delivery sheath, thus holding the plug tight into the outer end of the delivery sheath. The delivery sheath is long enough such that when its proximal end 343 contacts the proximal end of the femoral sheath 332, as shown in FIG. 11, the bleed back holes 344 are exposed to the blood flow in blood vessel lumen 336.

As shown in FIG. 12, the femoral sheath and plug assembly are then withdrawn until the bleed back blood flow stops. At this time, the plug and delivery sheath are at or proximal to the vessel wall 337. In an embodiment, the plug 340 occludes the blood flow into the wound tract opening and is released from the delivery sheath 341 at the same time that blood flow into the wound tract opening is prevented. In another embodiment, the whole assembly is then further withdrawn a fixed amount as shown in FIG. 13 to properly position the plug within the tissue tract proximal of the puncture in vessel wall 337, at which time the plug 340 is detached as previously described. A filler material, sealing fluid or other additional closure substance may then be added proximally of plug 340, if desired. A tether, such as a suture, may also be attached to the proximal portion of the plug to facilitate moving it or removing it from the patient's body after it has been detached.

As shown in FIG. 14, in a preferred embodiment, delivery sheath 235 is mounted on handle 239 which is provided with outlet tube 240 which is provided with port 241. Outlet tube 240 may be connected to a tubing (not shown) such as tubing/valve assembly 334 of FIG. 9. Thus, in such an embodiment, the blood flow through lumen 232 will be visible when it exits through port 241. Handle 239 is also provided with male fitting 237 which may be provided with threads in its distal region such that it can be brought into threaded engagement with the threads at the proximal portion 243 of plug introducer 236. Outlet tube 240 is located in slot 242 in handle 239 such that once bleed back flow stops when the femoral sheath and plug assembly are withdrawn to the point shown in FIG. 12, the slot defines the fixed amount to which the whole assembly comprising the femoral sheath delivery sheath and plug are further withdrawn prior to detachment of the plug as shown in FIG. 13.

The present invention is not to be considered to be limited to the specific embodiments set forth, but is of the full scope of the appended claims.

I claim:

1. A locator and closure device comprising
   an elongate member, said elongate member having a lumen, a distal opening and a proximal opening which are connected by the lumen and a distal portion with a substantially uniform outer diameter wherein said distal opening is located within said distal portion,
   said elongate member being adapted to be advanced through an introducer member to extend into a blood vessel of a patient such that said distal opening is located in the lumen of the blood vessel, and
   said device being provided with a bioabsorbable occlusion member releasably attached by an attachment formed by contact between said occlusion member and said elongate member at a specific position of said elongate member, in contact with said lumen of said elongate member and located distally of said distal opening, said occlusion member comprising an unrestrained maximal outer diameter configured to correspond to a diameter of a tissue passageway opening into said blood vessel lumen, said occlusion member configured to substantially block blood flow out of said blood vessel when released into the tissue passageway opening,
   wherein when said distal opening is located in the lumen of the blood vessel, blood can enter said distal opening without passing through said occlusion member, flow through said lumen, exit through said proximal opening and be visible outside of the patient's body.

2. The device of claim 1 wherein said occlusion member is expandable.

3. A method of installing a closure device for sealing a puncture in a blood vessel wall comprising the steps of
   introducing an elongate member through an introducer member disposed in a tract extending from said puncture to a patient's skin, said elongate member having a lumen, a first opening in its distal region, a second opening in its proximal region such that the lumen extends between said first opening and said second opening, said elongate member being provided with a bioabsorbable occlusion member located distally of said first opening such that said lumen of said elongate member contacts said occlusion member and wherein said elongate member has a distal portion with a substantially uniform outer diameter wherein said first opening is located within said distal portion and is adapted to extend into a blood vessel of a patient such that said occlusion member is fully inserted into the lumen of said blood vessel and said first opening is located in the lumen of the blood vessel such that blood entering said first opening without passing through said occlusion member, flowing through said lumen and exiting through said second opening is visible outside of the patient's body, and said occlusion member is releasably attached by an attachment formed by contact between said occlusion member and said elongate member at a specific position of said elongate member and wherein said occlusion member comprises an unrestrained maximal outer diameter configured to correspond to a diameter of a tissue passageway opening into said blood vessel lumen,
   advancing said elongate member until said first opening is located within the lumen of said blood vessel such that blood flows into said first opening and out of said second opening,
   withdrawing said elongate member until the flow of blood into said first opening is substantially prevented; and
   releasing said occlusion member from said elongated member within the tract to substantially block blood flow out of said blood vessel.

4. The method of claim 3 wherein releasing said occlusion member occurs at substantially the same time that blood flow into said first opening is substantially prevented.

5. A locator and closure device comprising
   an elongate member having a lumen and having a first opening in its distal region, wherein said distal region has a substantially uniform outer diameter, and a second opening in its proximal region such that the lumen extends between said first opening and said second opening;
   an occlusion member attached to a specific position of said distal region of said elongate member such that said lumen of said elongate member contacts said occlusion member and said occlusion member includes a bioabsorbable material and is distal from said first opening;
   said elongate member being adapted to be advanced through an introducer member to extend into a blood vessel of a patient such that said occlusion member is fully inserted into the lumen of said blood vessel and said first opening is located in the lumen of the blood vessel such that blood entering said first opening without passing through said occlusion member, flowing through said lumen and exiting through said second opening is visible outside of the patient's body, and said occlusion member is releasably attached by an attachment formed by contact between said occlusion member and said elongate member at a specific location on said elongate member and wherein said occlusion member comprises an unrestrained maximal outer diameter configured to correspond to a diameter of a tissue passageway opening into said blood vessel lumen, said occlusion member configured to substantially block blood flow out of said blood vessel when released into the tissue passageway opening.

6. The device of claim 5 wherein said occlusion member is expandable.

* * * * *